(12) United States Patent
Wada

(10) Patent No.: US 6,478,782 B1
(45) Date of Patent: Nov. 12, 2002

(54) ENEMA

(76) Inventor: Kaoru Wada, 12-905, 41, Nishishinjuku 4-chome, Shinjuku-ku, Tokyo (JP)

( * ) Notice: Subject to any disclaimer, the term of this patent is extended or adjusted under 35 U.S.C. 154(b) by 0 days.

(21) Appl. No.: 09/502,776

(22) Filed: Feb. 11, 2000

(51) Int. Cl.$^7$ .................................................. A61M 3/00
(52) U.S. Cl. ........................ 604/279; 604/117; 604/174; 604/179; 604/207; 604/248; 604/257; 4/420.1; 4/420.4; 4/443; 4/448
(58) Field of Search .............................. 604/73, 93.01, 604/117, 174, 179, 181, 207, 248, 257, 275, 278, 279

(56) References Cited

U.S. PATENT DOCUMENTS

| | | | | |
|---|---|---|---|---|
| 94,029 A | * | 8/1869 | Puffer | 604/257 |
| 650,080 A | * | 5/1900 | Marmaduke | 604/278 |
| 1,850,442 A | * | 3/1932 | Bradley | 604/174 |
| 1,911,229 A | * | 5/1933 | Gleim | 604/174 |
| 2,484,290 A | * | 10/1949 | Handel | 604/275 |
| 4,248,229 A | * | 2/1981 | Miller | 604/174 |

* cited by examiner

Primary Examiner—J. Casimer Jacyna
(74) Attorney, Agent, or Firm—Wenderoth, Lind & Ponack, L.L.P.

(57) ABSTRACT

An enema has liquid amount controlling component, namely a rotary valve, having an outer tube with a cylindrical concave part at its center and is provided with an insertion opening fitting a connecting tube and a discharge opening fitting a conduit on a side wall of the concave part of the outer tube. A rotator is provided with opening parts corresponding to the positions of the insertion opening and the discharge opening of the outer tube, and a knob part on an upper part of the rotator. Two fitting spring are integrally formed to extend on both sides of a fixture (8), and the fixture has a penetration hole for inserting a beak tube. The fixture slides on the said beak tube for controlling the length of the beak tube to be inserted into an anus. The rotator rotates in the outer tube according to the operation of the knob part of the rotator, and an amount of an injection liquid in a tank to be injected into the anus from the beak tube via the conduit is controlled according to the relationship between the opening parts of the rotator and the insertion opening and the discharge opening of the outer tube based on the rotation of the rotator.

11 Claims, 5 Drawing Sheets

ENEMA

BACKGROUND OF THE INVENTION

1. Field of the Invention

The present invention relates to an enema to be inserted into the anus of the human body to inject a fluid such as warm water into the intestines of the human body.

2. Statement of the Prior Art

An enema to be inserted into the anus has been constituted so as to inject a certain amount of a liquid, such as warm water and a chemical liquid, into the intestines to perform evacuation, and has been employed with a view towards improving fermentation in the intestines or to combat constipation.

Such an enema has been proposed in the official gazette of Japanese Utility Model Application No. 57-50043. The enema is provided, as shown in FIG. 5, with a thick grip 59 and a cock 58 at the central part of a conduit 52 connected to a tank 51 for controlling the amount of a liquid to be passed. The enema is also provided with a cock 50 as a liquid amount controlling part on a beak tube 53 fitted to the tip thereof. The enema is provided with the plurality of cocks 58, 50 to control the amount of the liquid to be injected. The enema is hard to operate, and since the grip part is unstable, it must be held with a hand at all times in applying the enema.

Thus, the conventional enema has disadvantages associated with the operation of the cocks and the inconvenience of requiring the use of hands during injection. Moreover, a patient cannot apply an enema without the help of a nursing person.

The present invention solves the conventional problems and provides an enema which enables a person to easily apply the enema to oneself without any help from a nursing person.

In addition, the present invention provides an enema which enables a person to easily perform intestinal washing continuously for oneself while sitting on a Western stool.

It is an object of the present invention to provide an enema which completely prevents liquid leakage from the liquid amount controlling component.

SUMMARY OF THE INVENTION

The above objects of the present invention can be accomplished by the constitution of an enema comprising a tank equipped with a suspender and a drop opening with a connecting tube fitting onto the bottom of the drop opening. A liquid amount controlling component is provided on the other end of the connecting tube connected to the drop opening, and a conduit is connected to the other end of the liquid amount controlling component. A beak tube to be inserted into the anus is provided on the tip of the conduit and fixing strings are provided on the connection part of the beak tube and the conduit. The liquid amount controlling component consists of an outer tube having a cylindrical concave part at the center and is provided with an insertion opening fitting the connecting tube and a discharge opening fitting the conduit on the side wall of the concave part. A rotator is closely fitted into the concave part of the outer tube and is provided with opening parts corresponding to the positions of the insertion opening and the discharge opening of the outer tube and a knob part on the upper part. A fixture provided with the fixing strings is slidably fitted to the beak tube, and the rotator rotates in the outer tube according to the operation of the knob part of the rotator. The amount of an injection liquid in the tank to be injected into the anus from the beak tube via the conduit is controlled by the opening part of the rotator, and the insertion opening and the discharge opening of the outer tube according to the rotation.

Moreover, the above object can be accomplished by the constitution of an enema, wherein the fitting strings are integrally formed to extend on both sides of the fixture, and a penetration hole for the insertion of the beak tube is provided on the fixture. Further, by the constitution of an enema, wherein a suction device to be fixed to a stool is provided on the outer periphery of the connecting tube or the conduit connected to the liquid amount controlling component.

Further, the above object can be accomplished by the constitution of an enema, wherein the outer tube and the rotator of the liquid amount controlling component are formed of a rather elastic synthetic resin. Further, by the constitution of an enema, wherein a concave part and a convex part engaging with each other are formed on the inner wall side of the outer tube of the liquid amount controlling component and the outer wall side of the rotator, respectively.

Since the enema of the present invention is provided with a liquid amount controlling component that easily operates a knob part between a connecting tube and a conduit, the amount of a liquid to be injected can be easily controlled by the rotation of the knob part. In addition, not only is the enema easy to use with the operation of the knob, but the knob can also surely control the amount of a liquid.

In particular, since the liquid amount controlling component is formed of a synthetic resin elastic material, the enema has excellent adhesion between the outer tube and the rotator and is free of liquid leakage. In addition, the rotator and the outer tube are provided with a closely engaging concave-convex mechanism and a packing, which can completely prevent the leakage of an injection liquid.

BRIEF DESCRIPTION OF THE DRAWINGS

FIG. 3(a) is a perspective view showing the combination state of the beak tube and the fixture.

DETAILED DESCRIPTION OF THE INVENTION

Figure 1:
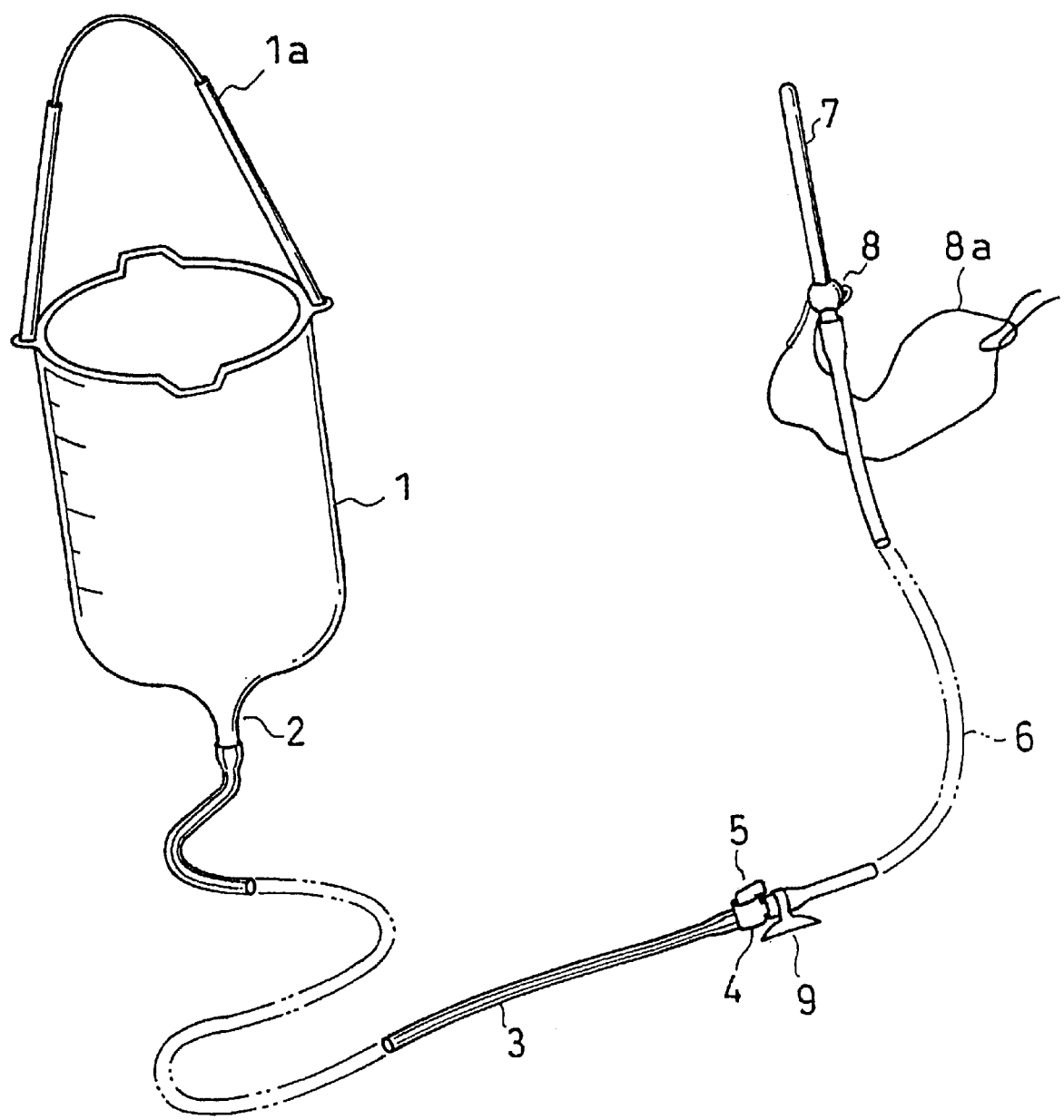
FIG. 1 is a schematic perspective view showing a whole view of an enema of the present invention.
Figure 2:
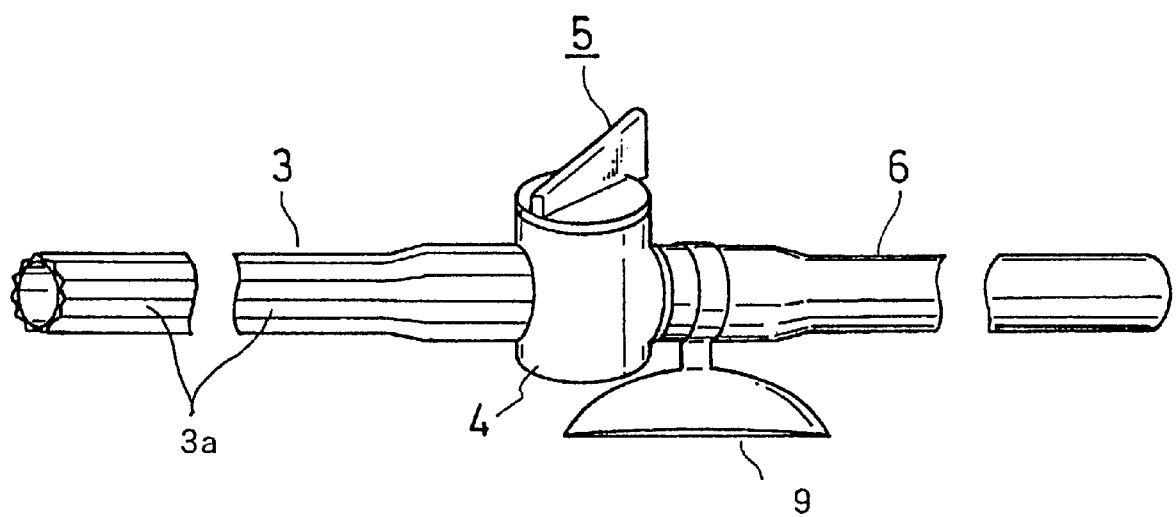
FIG. 2 is an enlarged perspective view of a main part of the enema of the present invention.

Hereunder, the enema of the present invention will be described according to the embodiment shown in the drawings.

In FIG. 1, the upper part of a tank 1 filled with an enema liquid such as warm water is open. A suspender 1a for suspending the tank 1 is additionally provided on a shoulder part of the tank 1, and a drop opening 2 is provided on the bottom of the tank 1. The capacity of the tank 1 is about 6 liters. A connecting tube 3 is connected to the drop opening 2, and an insertion opening 4a of an outer tube 4 of a cock as a liquid amount controlling component is fitted to the other end of the connecting tube 3. The connecting tube 3 is formed of a transparent synthetic resin so that the flow of an injection liquid inside of the connecting tube 3 can be observed, and the outer side of the connecting tube 3 has longitudinal grooves 3a. A conduit 6 is fitted to a discharge opening 4b provided on the outer tube 4. The conduit 6 is formed of a rubber tube. A beak tube 7 to be inserted into the anus for injecting an injection liquid into the intestines is connected to a tip of the conduit 6. A fixture 8 integrally formed with. fixing strings 8a extending from both sides of the fixture is fitted to the beak tube 7.

Figure 4:
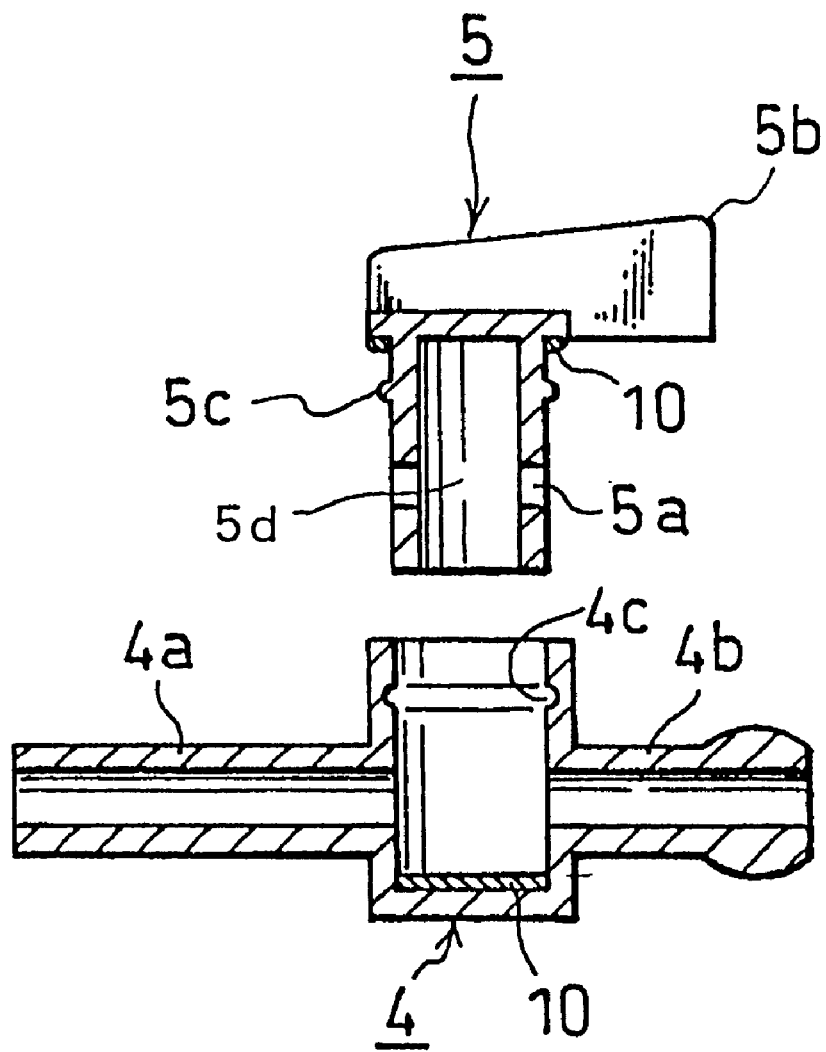
FIG. 4 is an analysis longitudinal sectional view of one embodiment of a liquid amount controlling component to be employed in the enema of the present invention.
Figure 5:
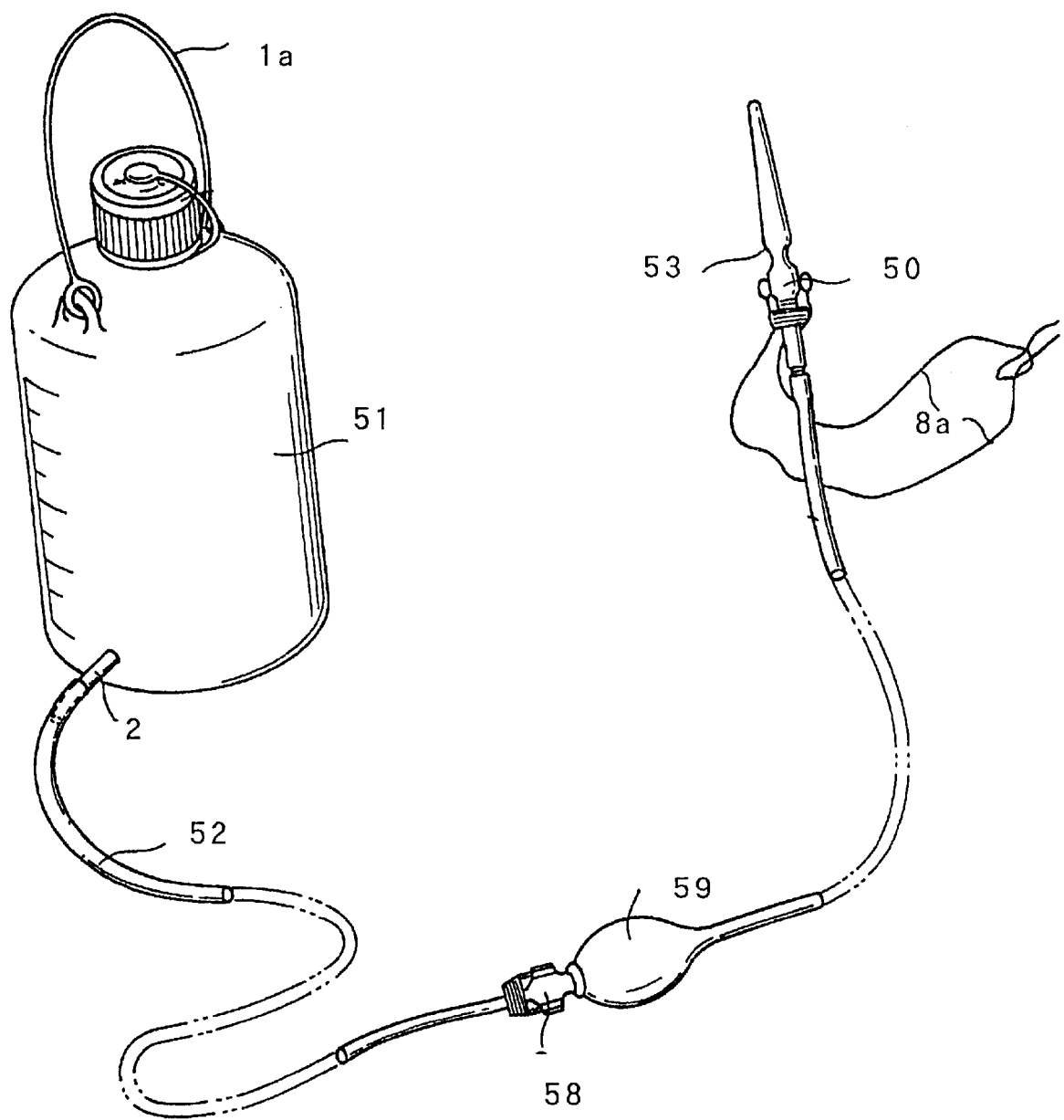
FIG. 5 is a whole view of a conventional enema.

A control valve 5 having a knob 5b as a rotator is fitted to the outer tube 4. The control valve 5 is provided with a penetration hole 5a suitable for the insertion opening 4a and the discharge opening 4b of the outer tube 4. With a view towards improving the closeness of the control valve 5 and the outer tube 4 to prevent the leakage of an injection liquid, an engagement groove 4c and an engagement protrusion 5c are respectively provided on the closed parts of the outer tube 4 and the control valve 5. Moreover, a packing 10 may be provided between both the outer tube 4 and the control valve 5. The outer tube 4 and the control valve 5 are produced from a synthetic resin, such as an ethylene-based resin, having elasticity. A cave 5d formed into a cylindrical state with a hollowed central part is provided in the control valve 5, as shown in FIG. 4.

Figure 3:
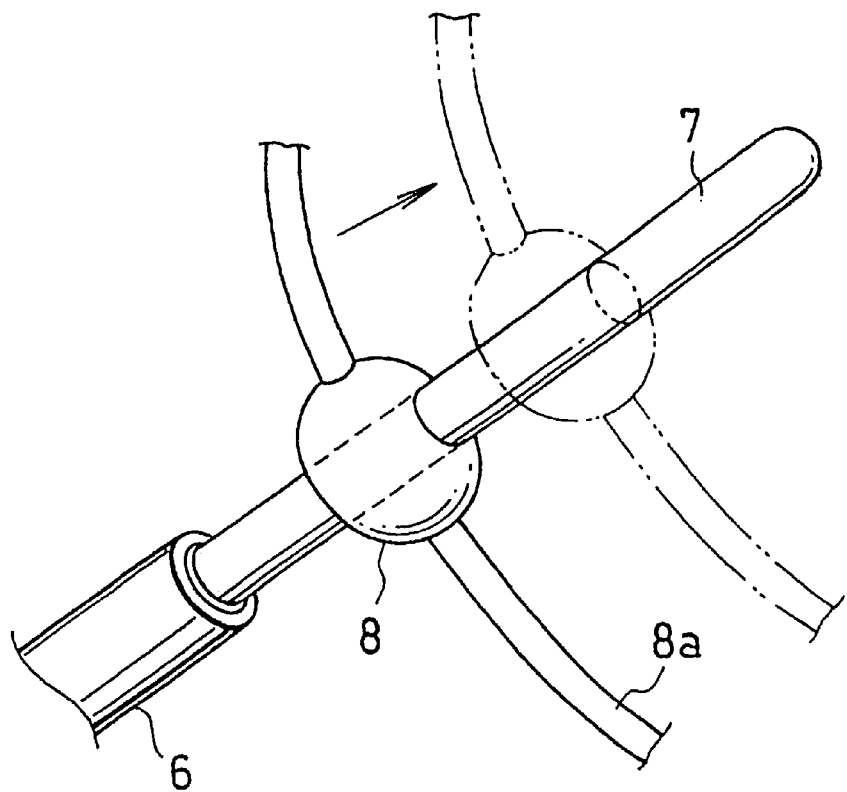
FIGS. 3(a) and (b) show one embodiment of a beak tube and a fixture to be employed in the present invention.
FIG. 3(b) is an enlarged perspective view of the fixture.
Figure 3:
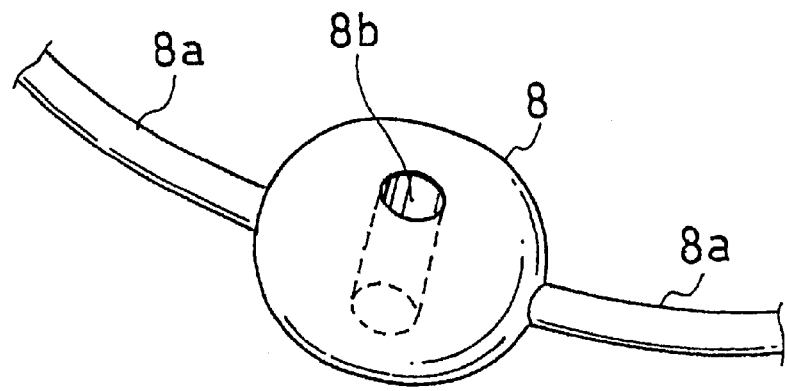

The beak tube 7 is fitted to the tip of the conduit 6. On the fixture 8 having a penetration hole 8b to be penetrated by the beak tube 7 are provided the fixing strings 8a extending to both sides so that the beak tube 7 can be inserted into the penetration hole 8b of the fixture 8 to slidably fit, thereby enabling control of the length of the insertion of the beak tube 7 into the anus (see the dotted line of FIG. 3(a)). The beak tube 7 is formed of a soft component so as not to injure the skin of the inner wall of the anus, and, for example, a polyurethane resin is preferably employed. The two fixing strings 8a and the fixture 8 are integrally formed, and the fixture 8 and the fixing strings 8a are formed of a synthetic resin so that they can be easily washed. A suction device 9 is provided on the conduit 6 connected to the outer tube 4, and the suction device 9 can be fixedly adhered to a stool.

A method of using the enema of the present invention having the above constitution will be described.

The penetration hole 5a of the control valve 5 is placed into a state separated from the position of the insertion opening 4a of the outer tube 4, namely, the control valve 5 is in a closed state, by operating the knob 5b of the control valve 5 of the cock provided between the connecting tube 3 and the conduit 6. A prescribed amount of an injection liquid such as warm water is introduced from the upper opening of the tank 1 when the control valve 5 is in such a state. The suspender 1a additionally provided on the tank 1 is suspended on an upper spot such as a shelf.

Subsequently, the beak tube 7 is inserted into the anus with one's own hand, and the fixing strings 8a are placed on the stool and pressed with the buttocks such that the fixed strings 8a are surely fixed. Moreover, upon demand, the fixing strings 8a can be bound to the stool or the thigh to fix and support the beak tube 7 at the position of the anus. The penetration hole 5a is slowly positioned to be aligned with the insertion opening 4a and the discharge opening 4b by rotating the knob 5b of the control valve 5 of the cock, and the injection liquid is inserted into the intestines in a wholly open state.

Evacuation is performed naturally while the beak tube 7 is inserted into the anus when a prescribed amount of the ejection liquid is injected into the intestines. Feces contained in the intestines are discharged by repeating the operation of the enema ten or several times, or from 20 to 30 times. When the injection liquid in the tank 1 is completely used, the knob 5b of the cock is turned to operate the control valve 5 and to move the penetration hole 5a to cut off its alignment with the insertion opening 4a and discharge opening 4b.

The enema of the present invention is easy to operate with one hand since the liquid amount controlling component is provided at one spot. Further, the operation of the control valve 5 can surely be performed since the position of the cock is fixed by the suction device 9. Moreover, since the connecting tube 3 is formed of a transparent synthetic resin, the state of the injection liquid passing can be observed, and the amount of the injection liquid injected is easily controlled. Since the connecting tube 3 has flexibility and longitudinal grooves 3a are provided on the surface thereof, the sureness in handling is good, and the connecting tube 3 has good durability.

Moreover, since the cave 5d is provided on the control valve 5 of the cock, the standing of the injection liquid occurs and a rapid liquid flow is controlled. At the same time, the cock has elasticity due to the presence of the cave 5d, and the outer periphery face of the control valve 5 and the inner wall of the outer tube 4 are closely fitted.

EFFECTS OF THE INVENTION

The enema of the present invention has a simple constitution and can be easily operated for oneself while sitting on a Western stool. Moreover, not only can the amount of a liquid injected be easily controlled, but the user is utterly free of worry of liquid leakage, since the liquid amount controlling component consists of an outer tube of a cock having a knob and a control valve closely adhered to each other.

In addition, since a beak tube of the enema is inserted into the anus and the insertion position is surely fixed with fixing strings, it is possible to maintain the inserted state of the beak tube with both hands free for several washing operations of the intestines. Moreover, since a suction device is provided near the cock, the control of the injection liquid can surely be performed.

What is claimed is:

1. An enema comprising:

a tank;

a connecting tube having a first end and a second end, said first end of said connecting tube being connected to said tank;

a rotary valve having a first end and a second end, said first end of said rotary valve being connected to said second end of said connecting tube;

a conduit having a first end and a tip opposite to said first end of said conduit, said first end of said conduit being connected to said second end of said rotary valve;

a beak tube being adapted for insertion into an anus, said beak tube being provided at said tip of said conduit; and a fixture having a pair of fixing strings and a penetration hole, said fixture being slidably fitted on said beak tube via said penetration hole, wherein said rotary valve comprises an outer tube having a cylindrical concave part at a center of said outer tube, a sidewall of said cylindrical concave part being provided with an insertion opening fitting with said connecting tube and a discharge opening fitting with said conduit, and a rotator being closely fitted into said cylindrical concave part of said outer tube, said rotator having openings corresponding to positions of said insertion opening and said discharge opening of said outer tube and a knob part on an upper part of said rotator, and said rotator being rotatable within said outer tube by operating said knob part, said rotator being operable to control an amount of injection liquid located in said tank to be injected into the anus via said beak tube based on an alignment between said openings of said rotator and said insertion opening and said discharge opening of said outer tube, and wherein said pair of fixing strings are integrally formed to extend from opposite sides of said fixture, said fixture being operable to control a length of said beak tube to be inserted into the anus by slidably positioning said fixture along said break tube, and said fixing strings being operable to fix said fixture by being placed on a surface and sat on.

2. An enema according to claim 1, further comprising a suction device connected to one of an outer periphery of said connecting tube and an outer periphery of said conduit, said suction device being operable to be fixed to a surface.

3. An enema according to claim 2, wherein said rotator and said outer tube are formed from an elastic synthetic resin.

4. An enema according to claim 2, wherein an outer wall side of said rotator forms a convex part engaging with an inner wall side of said cylindrical concave part of said outer tube.

5. An enema according to claim 1, wherein said rotator and said outer tube are formed from an elastic synthetic resin.

6. An enema according to claim 5, wherein an outer wall side of said rotator forms a convex part engaging with an inner wall side said cylindrical concave part of said outer tube.

7. An enema according to claim 1, wherein an outer wall side of said rotator forms a convex part engaging with an inner wall side of said cylindrical concave part of said outer tube.

8. An enema according to claim 7, wherein said rotator and said outer tube are formed from an elastic synthetic resin.

9. An enema according to claim 1, wherein said tank has a suspender and a drop opening, said first end of said connecting tube being connected to said drop opening.

10. An enema according to claim 1, wherein an inner wall side of said cylindrical concave part of said outer tube has an engaging groove, and an outer wall side of said rotator has an engagement protrusion corresponding to said engaging groove in order to maintain said rotator within said outer tube and to prevent the injection liquid from leaking between said rotator and said outer tube.

11. An enema according to claim 1, further comprising packing located around an outer wall side of said rotator, said packing being operable to prevent the injection liquid from leaking between said rotator and said outer tube.

* * * * *